(12) United States Patent
Calatzis et al.

(10) Patent No.: US 8,591,816 B2
(45) Date of Patent: *Nov. 26, 2013

(54) CARTRIDGE DEVICE FOR BLOOD ANALYSIS

(75) Inventors: Andreas Calatzis, Munich (DE); Ben Krüger, Munich (DE); Marc Wittwer, Munich (DE)

(73) Assignee: F. Hoffmann-La Roche AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/029,553

(22) Filed: Feb. 17, 2011

(65) Prior Publication Data

US 2011/0133762 A1 Jun. 9, 2011

Related U.S. Application Data

(62) Division of application No. 10/583,062, filed as application No. PCT/EP03/14329 on Dec. 16, 2003, now Pat. No. 7,901,629.

(51) Int. Cl.
*G01N 33/86* (2006.01)
*G01N 33/48* (2006.01)
*G01N 27/02* (2006.01)
*B01L 3/00* (2006.01)

(52) U.S. Cl.
USPC ...... 422/73; 422/68.1; 422/82.01; 422/82.02; 422/547; 422/554; 436/63; 436/69; 436/149; 436/150; 436/151; 600/369; 73/64.41; 324/722

(58) Field of Classification Search
USPC .......... 436/63, 69, 73, 80, 149, 150, 151; 422/68.1, 73, 82.01, 82.02, 500, 547, 422/549, 554; 600/369; 73/64.41; 324/722
See application file for complete search history.

(56) References Cited

U.S. PATENT DOCUMENTS 2,555,937 A 6/1951 Rosenthal et al.
3,674,012 A 7/1972 Sage
(Continued)

FOREIGN PATENT DOCUMENTS

DE 331 410 C 1/1921
EP 0909949 4/1999
(Continued)

OTHER PUBLICATIONS

Webster's Ninth New Collegiate Dictionary, 1990, pp. 603 and 1003.*

(Continued)

*Primary Examiner* — Maureen Wallenhorst
(74) *Attorney, Agent, or Firm* — Jenkins, Wilson, Taylor & Hunt, P.A.

(57) ABSTRACT

A cartridge device having a receiving portion for receiving a blood sample and a jack portion for receiving a plug; a stirring device for circulating the blood sample within the receiving portion; and an electrode holder having at least one incorporated electrode wire pair; wherein the electrode holder is attachable to the cell such that one end of the at least one electrode wire pair forms a sensor unit for measuring the electrical impedance between the two electrode wires of the at least one electrode wire pair within the blood sample and that the opposite end of the at least one electrode wire pair forms a plug portion being connectable directly to the plug for an electrical connection of the sensor unit to an analyzer.

21 Claims, 10 Drawing Sheets

(56) References Cited

U.S. PATENT DOCUMENTS

| | | | |
|---|---|---|---|
| 3,699,437 | A | 10/1972 | Ur |
| 3,840,806 | A | 10/1974 | Stoner et al. |
| 4,123,701 | A | 10/1978 | Josefsen et al. |
| 4,319,194 | A | 3/1982 | Cardinal et al. |
| 4,591,793 | A | 5/1986 | Freilich |
| 4,604,894 | A | 8/1986 | Kratzer et al. |
| 5,491,408 | A | 2/1996 | Rousseau |
| 5,922,551 | A | 7/1999 | Durbin et al. |
| 6,004,818 | A | 12/1999 | Freilich et al. |
| 6,010,911 | A | 1/2000 | Baugh et al. |
| 6,046,051 | A | 4/2000 | Jina |
| 6,584,349 | B1 | 6/2003 | Sage et al. |
| 7,021,122 | B1 | 4/2006 | Rosemberg et al. |
| 7,291,310 | B2 | 11/2007 | Martin et al. |
| 7,901,629 | B2 * | 3/2011 | Calatzis et al. ............ 422/73 |
| 8,465,978 | B2 | 6/2013 | Calatzis et al. |
| 2011/0136164 | A1 | 6/2011 | Calatzis et al. |

FOREIGN PATENT DOCUMENTS

| | | |
|---|---|---|
| GB | 2049199 A | 4/1980 |
| WO | WO 02/25277 A1 | 3/2002 |

OTHER PUBLICATIONS

International Search Report corresponding to PCT application No. PCT/EP 03/14329 dated Oct. 6, 2004.
Office Action/Restriction Requirement for U.S. Appl. No. 10/583,062 dated Mar. 23, 2010.
Non-Final Office Action for U.S. Appl. No. 10/583,062 dated May 7, 2010.
Non-Final Office Action for U.S. Appl. No. 13/029,575 dated Jun. 13, 2011.
Canadian Office Action for Application No. 2,547,544 dated Nov. 23, 2011.
Final Office Action for U.S. Appl. No. 13/029,575 dated Dec. 23, 2011.
Non-Final Office Action for U.S. Appl. No. 13/029,575 dated May 30, 2012.
Canadian Notice of Allowance for Application No. 2,547,544 dated Jun. 7, 2012.
Notice of Allowance for U.S. Appl. No. 13/029,575 dated Sep. 14, 2012.
Notice of Allowance for U.S. Appl. No. 13/029,575 dated Feb. 25, 2013.

* cited by examiner

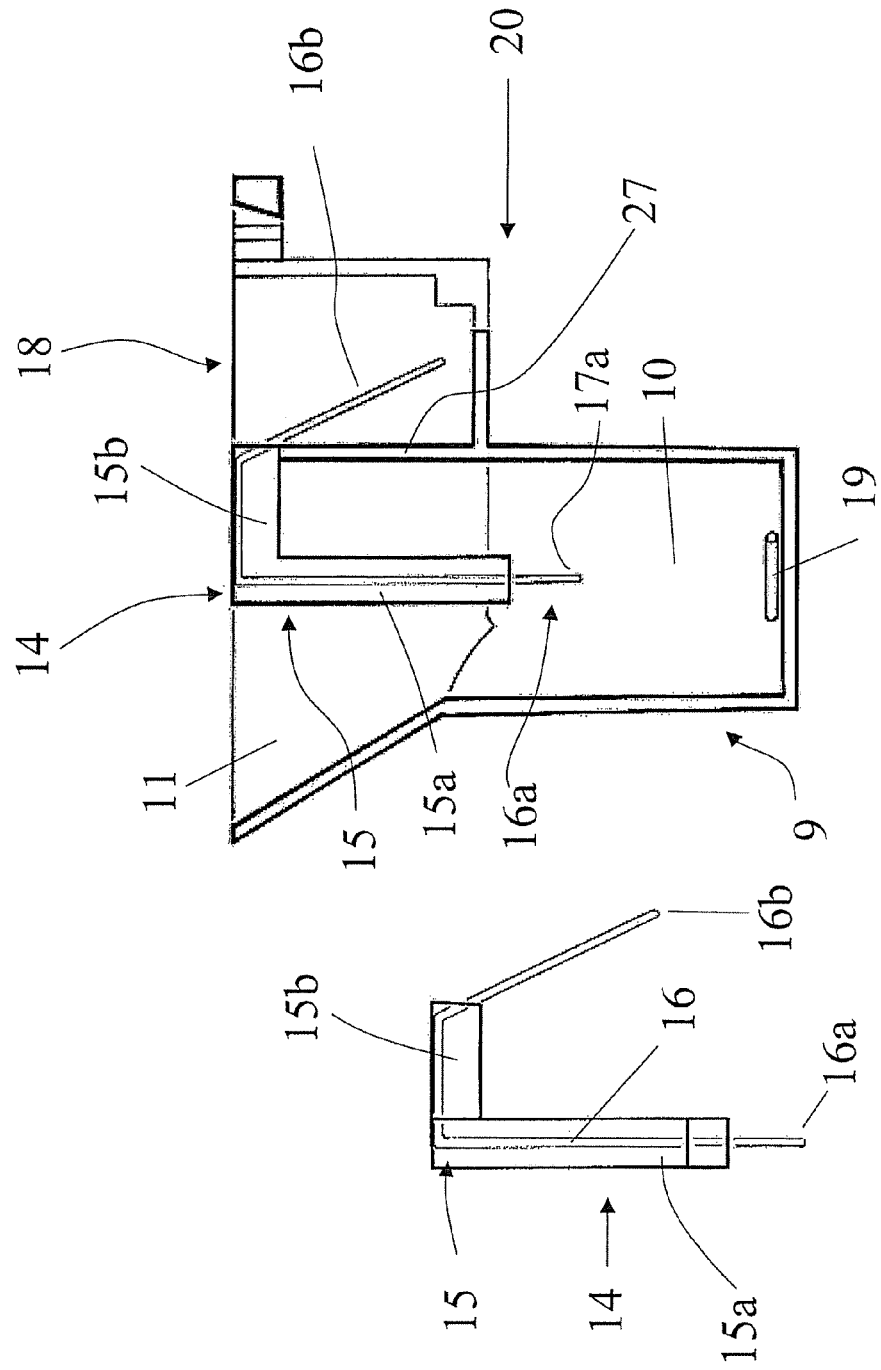

CARTRIDGE DEVICE FOR BLOOD ANALYSIS

CROSS REFERENCE TO RELATED APPLICATIONS

This application is a divisional application which claims the benefit of and priority to U.S. utility patent application Ser. No. 10/583,062 filed Jan. 31, 2007, now U.S. Pat. No. 7,901,629, issued on Mar. 8, 2011, which claims priority to PCT/EP2003/014329 filed Dec. 16, 2003, the entire contents of which are hereby incorporated by reference herein.

TECHNICAL FIELD

The present invention relates to a cartridge device for blood analysis and a method for testing platelet functions.

BACKGROUND ART

Though the present invention can be used in many fields of measuring fluids it will be described in regard to measuring the platelet function of blood in the following.

Blood consists of cells suspended in so called plasma, a protein rich fluid. The major groups of cells in the blood are red cells, white cells and platelets. The platelets are responsible for plugging gaps or holes in the blood vessel wall. This is achieved by a mechanism called aggregation-adhesion reaction. When the platelets aggregate, they become sticky and, as a result thereof, they stick to each another and to the damaged tissue. Usually this happens when the platelets come into contact with certain materials and chemicals, especially those related to damaged cells.

Platelet adhesion to injured blood vessels is an essential property in order to close wounds and thus to ensure survival of the organism after for example a trauma. However the adhesion and aggregation of platelets can also be extremely dangerous when the platelets mistake an aged or inflamed vessel for a vascular injury and thus impair blood flow in tissues of vital importance. Such processes take place during a myocardial infarction or a stroke, diseases which account for more deaths in the industrialised nations than infectious diseases or cancer.

An increasing number of patients who have suffered myocardial infarction or stroke as well as patients who are at high risk for these events is treated for a reduced tendency of their platelets to aggregate with substances called "anti-platelet agents". Besides their beneficial effect—to reduce the incidence of platelets closing vitally important vessels—these drugs may also induce bleeding. However a larger danger is due to the fact that in some of the patients the drugs seem not to work properly. Current studies have shown that up to 25% of the patients treated do not adequately respond to this treatment.

It is thus not only of scientific interest, but also of high clinical importance to be able to test the function of the platelets and the individual response to drugs which interfere with their activation. Several techniques according to the prior art are used to analyse platelet functions or the action of anti-platelet drugs.

An early but still widely used development is the Born aggregometer which measures the change of light transmission of platelet-rich plasma (PRP) during the process of aggregation. Platelet rich-plasma is obtained by centrifugation of anticoagulated blood at a relatively low speed, which removes the heavy (hemoglobin-filled) red cells from the plasma, but leaves the much lighter platelets in the solution. Because of the platelet content the light transmission of PRP is relatively low. When the platelets aggregate the optical density is reduced, because the platelets form few large aggregates, which interfere much less with the light transmitted through the sample.

A disadvantage of this technique is the necessity of producing PRP, whose extraction is a complicated, time-consuming and thus expensive procedure. Furthermore, the aggregation of platelets is not measured in its natural environment, blood, thus the influence of red and white cells on the platelets is not measured.

Other methods disclosed in documents U.S. Pat. No. 4,604,894 of Kratzer and Born, U.S. Pat. No. 6,010,911 of Baugh et al. and U.S. Pat. No. 5,922,551 of Durbin et al. require relatively complex and expensive cartridges interfering with the use of these techniques for routine testing.

Document U.S. Pat. No. 4,319,194 of Cardinal et al. discloses a platelet aggregation analysis typically performed in whole blood by measuring the electric impedance between two electrodes, being immersed in a sample. During initial contact with the blood or PRP, the electrodes are coated with a monolayer of platelets. When an aggregating agent is added, platelets gradually accumulate on the monolayer coating, increasing the impedance between the electrodes. The change in impedance is recorded as a function of time. It is preferred that the electrodes comprise precious metals since base metals drift in blood-saline mixtures.

One disadvantage of precious metal electrodes is high costs. Hence they are too expensive to be disposable. Therefore, the electrode assembly must be cleaned by hand between tests, exposing the operator to contact with the sample, and thus potentially exposing the operator to diseases transmitted through the fluids contained in the sample. Since diseases such as hepatitis and AIDS can be transmitted through handling of blood products, there is an understandable reluctance on the part of medical professionals to handle blood, blood products and objects contamined therewith.

A further disadvantage of this structure is due to the fact that the electrodes of the aggregometer have to be handled by the user during the cleaning procedure, potentially disturbing the adjustment of the distance between the electrodes, causing inconsistent results. Furthermore each electrode requires exact placement of the wires during fabrication, making the final product expensive.

Document U.S. Pat. No. 4,591,793 of Freilich describes a substitution of the wire electrodes by a conductive ink printed on a plastic non-reactive base.

However this device is detrimental due to the fact that the platelets have difficulties in adhering to the exposed conductive surface of the Freilich device. Sometimes the aggregated platelets break off the surface, causing a sudden change in impedance. Hence the measured results by the device are inconsistent and not reproducible.

A further measuring cell assembly according to the prior art is disclosed in Document U.S. Pat. No. 6,004,818 of Freilich et al., which is shown in FIGS. 11A and 11B.

FIG. 11A illustrates an explosive view of a part of a measuring cell device comprising an insulator 1, which is sandwiched between two flag-shaped electrodes 2. Each electrode 2 includes a connection tab 3 at one end and a tip 4 at the other end thereof, with a shaft 5 joining the tab 3 and the tip 4 respectively. After joining the two electrodes 2 and insulator 1 together a non-conductive coating is applied to the insulator 1 and to the electrode shafts 5.

FIG. 11B illustrates a perspective view of a measuring cell device according to the prior art. As shown in FIG. 11B the electrode assembly is fixed within a cuvette 56 using a positional clip 7. Prior to and during measurement, a stir bar 8 is activated to generate a circular flow of sample within the cuvette 6.

One drawback of the aforementioned measuring cell device is the use of punched sheet metal for the electrodes 2. The outline of the electrodes can economically be produced by the process of punching or related methods. However the surface qualities produced by these methods are relatively poor and vary during the production of large quantities (because of the aging of the punching blades applied during the process). The quality of the surfaces, which strongly affect the measurement, are thus strongly varying resulting in high variations between different disposable electrodes.

A further disadvantage is due to the fact that the complete measuring cell device consists of six different pieces, namely the two electrodes 3, the insulator 1, the coating, a cuvette 6, a positional clip 7 and a stir bar 8. This results in an expensive, complicated production process, which is either labor intensive or requires high investments for an automated assembly line.

Additionally the measuring cell device of Freilich does not overcome the relatively high variation reported for whole blood aggregometry. In document U.S. Pat. No. 6,004,818 a variation of around 10-15% between multiple measurements is reported for said measuring cell assembly.

SUMMARY OF THE INVENTION

Hence it is an object of the present invention to provide a cartridge device which overcomes the above mentioned drawbacks, particularly to provide a cartridge device which is economical, reproducible, safe and easy to use.

It is another object of the present invention to eliminate the limited reproducibility of previous methods according to the prior art for the measurement of aggregation in whole blood.

It is still another object of the present invention to provide a cartridge device which is accurate and so economical to produce that it can be discarded after each test.

It is still another object of the present invention to provide a cartridge device which can be provided ready to use, so the application of the technique is simple and contains only few user-related sources of error and variation.

The present invention provides a cartridge device for analysing blood comprising a cell having a receiving portion for receiving a blood sample and a jack portion for receiving a plug; a stirring device for circulating said blood sample within said receiving portion; and an electrode holder having at least one incorporated electrode wire pair; wherein the electrode holder is attachable to the cell such that one end of the at least one electrode wire pair forms a sensor unit for measuring the electrical impedance between the two electrode wires of the at least one electrode wire pair within the blood sample and that the opposite end of the at least one electrode wire pair forms a plug portion being connectable directly to the plug for an electrical connection of the sensor unit to an analyser.

Furthermore the present invention provides a cartridge device for analysing blood comprising a cell having a receiving portion for receiving a blood sample; a stirring device for circulating said blood sample within said receiving portion; and at least two electrodes for measuring the electrical impedance between the at least two electrodes within the blood sample; wherein the at least two electrodes consist of a metal comprising a first material with a high electrical conductivity, which is covered by a second material, which has a high electrical conductivity and which is resistant against oxidation.

Additionally the present invention provides a method for analysing blood by means of a cartridge device comprising at least three electrode wires or electrodes for measuring the electrical impedance between at least two of the at least three electrode wires or electrodes, comprising the following steps: measuring the electrical impedance between at least two different pairs of electrode wires or electrodes; comparing the measured electrical impedance values; discarding and repeating the measurements in case the variation is outside a predetermined threshold range; or indicating the measured electrical impedance values and/or the mean value thereof in case the variation is within the predetermined threshold range.

The dependent claims disclose further features and advantages of the present invention.

Hence the present invention provides a disposable device which overcomes the main problems of the aforementioned developments. The apparatus measures the change of impedance during the process of aggregation, whereas the quality of the measurement is ensured by a double-, triple- or multi-determination of the impedance. The cartridge can be manufactured at very low costs and is well suited for full automation of the production process.

The device for monitoring blood-platelet aggregation comprises a cartridge including electrodes; a means for stirring the sample; a power source for supplying electric current to the electrodes; and a data analysis device for receiving and analysing the change in electrical resistance or impedance between the electrodes.

A device is provided which is economical, accurate and quality-controlled. The test includes a disposable test cell having preferably at least two separate sensor elements. Each sensor element consists of preferably at least two separate conductive elements. During the analysis blood is placed in the test cell. By adequate means it is stirred. Optionally reagents activating or inhibiting platelet function are added. When blood platelets are activated they adhere on the conductive elements and alter electrical variables measured e.g. the resistance between the conductive elements or the electrical impedance. By comparing the values assessed on the different electrodes the result of the analysis is being controlled. When an adequate accordance between the individual results is attained, the result is accepted and the value or the mean (or median) value of the results is reported. If highly discrepant results are determined the analysis is rejected and a repeated analysis is requested.

The present invention further describes an economical and standardized production technique using injection moulding providing an improved analytical signal using suitable electrode compositions. The conductive elements are formed by wires which incorporate two functions. In their upper part they form a connector—or jack—by which the conductivity signal is detected. In the lower part they are contacted with the blood sample and serve as a sensor for the platelet aggregation. The conductive elements are formed from a material of high conductivity and precious surface. A silver-copper material coated by silver or other precious material is preferably applied. This leads to a strong signal, due to the higher difference in conductivity between the platelet-coated vs. the uncoated electrode. In addition also the detection of the conductivity over the connector—or jack—is improved.

Hence the present invention allows to asses the whole blood aggregation in a routine setting. Unlike previously applied methods for the assessment of whole blood aggregation it is easy to use and does not require the cleaning of blood-contaminated devices. Compared to the measurement of aggregation in platelet rich plasma the inventive method provides the advantage to eliminate the need to centrifuge blood to obtain PRP for use in measuring aggregation of platelets optically. Thus reduced labor costs, increased speed, and test of the platelets in their natural milieu are important advantages. The measurement in whole blood also allows studies to be performed in cases where optical aggregation is not reliable, such as giant platelets (Bernard-Soulier syndrome), where red cells have been lysed or where it is difficult to obtain enough blood to make PRP, such as with small animals or babies.

In addition whole blood aggregometry has the advantage that—like the Born aggregometry—it provides a continuous signal of the kinetics of platelet aggregation, unlike other methods, which provide only a measure for total aggregation, without revealing the kinetics of the process.

BRIEF DESCRIPTION OF THE DRAWINGS

The invention may be further understood by reference to the drawings, wherein:

FIG. 3 is a side view of an electrode holder according to certain embodiments of the present invention (double, linear triple or linear quadruple detection technique);

FIG. 4 is a side view of the cartridge according to certain embodiments of the present invention (double, linear triple or linear quadruple detection technique);

DETAILED DESCRIPTION OF THE INVENTION

Figure 1:
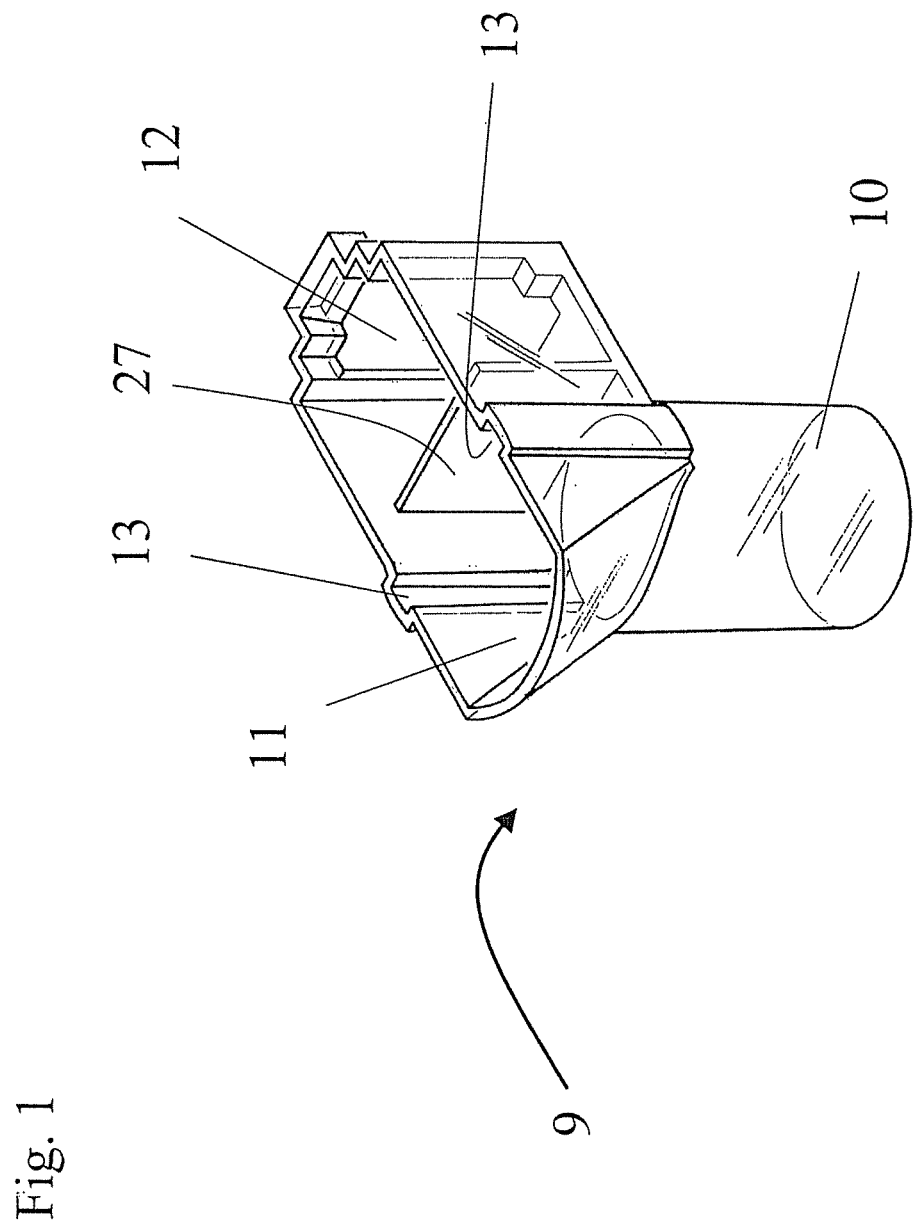
FIG. 1 is a perspective view of a cell according to an embodiment of the present invention.

In all figures like reference numerals are used to demote like elements and/or like functions of respective elements as long as nothing else is stated. It should be noticed that in the following the term cartridge describes the disposable structure applied in preferred embodiments of the invention. It consists of a cell 9 and an electrode holder 14.

In a preferred embodiment the cartridge device 20 consists of two main parts 9 and 14 made by particularly injection moulding. The one part is a single pieced receiving means and subsequently called cell 9.

FIG. 1 depicts a cell 9 in a perspective view according to a preferred embodiment of the present invention. The cell 9 comprises at least a preferably cylindrical receiving portion or cup portion 10, which is open at one face side, holding a sample during the analysis. The sample is placed into the cup portion 10 of the cell 9 by means of a particularly conical funnel tube 11.

The cell 9 further comprises a jack portion 12 adjacent to the cup portion 10 and separated therefrom by a stopping wall 27. Together with an electrode holder 14, described later in further details (see FIG. 2), the jack portion 12 forms a jack 18 (see FIG. 3), in which a plug 22 (described later in further details) is arranged and which allows the electrical connection of the cell 9 to an instrument, for example an analyser.

A guiding rail 13 is formed on both sides of the funnel tube 11 of the cell 9, respectively, for guiding the electrode holder 14 into a secure and tight connection with the cell 9 as shown in FIG. 4.

Preferably and as shown in FIG. 1 the whole cell 9 is formed in a way that it can be easily unmoulded with a two part injection moulding mould. This requires that the cup 9 does not form any undercuts and that the outer and inner surfaces are at least slightly conical. Although the cell 9 has three different functional portions, it can inexpensively be produced as one part using injection moulding. This minimises production costs on the one hand and the need for manual handling for the use on the other hand.

The cell 9 is in particular produced of blood compatible material such as polystyrene. Other usable materials are polymethyl methacrylate (PMMA) or polyethylene. The importance of using a blood compatible material is that the blood platelets will not get activated by the contact with the cell material. This allows to activate specifically the platelets as intended for the different test methods performed.

Dual Electrode Cartridge Device

Figure 2:
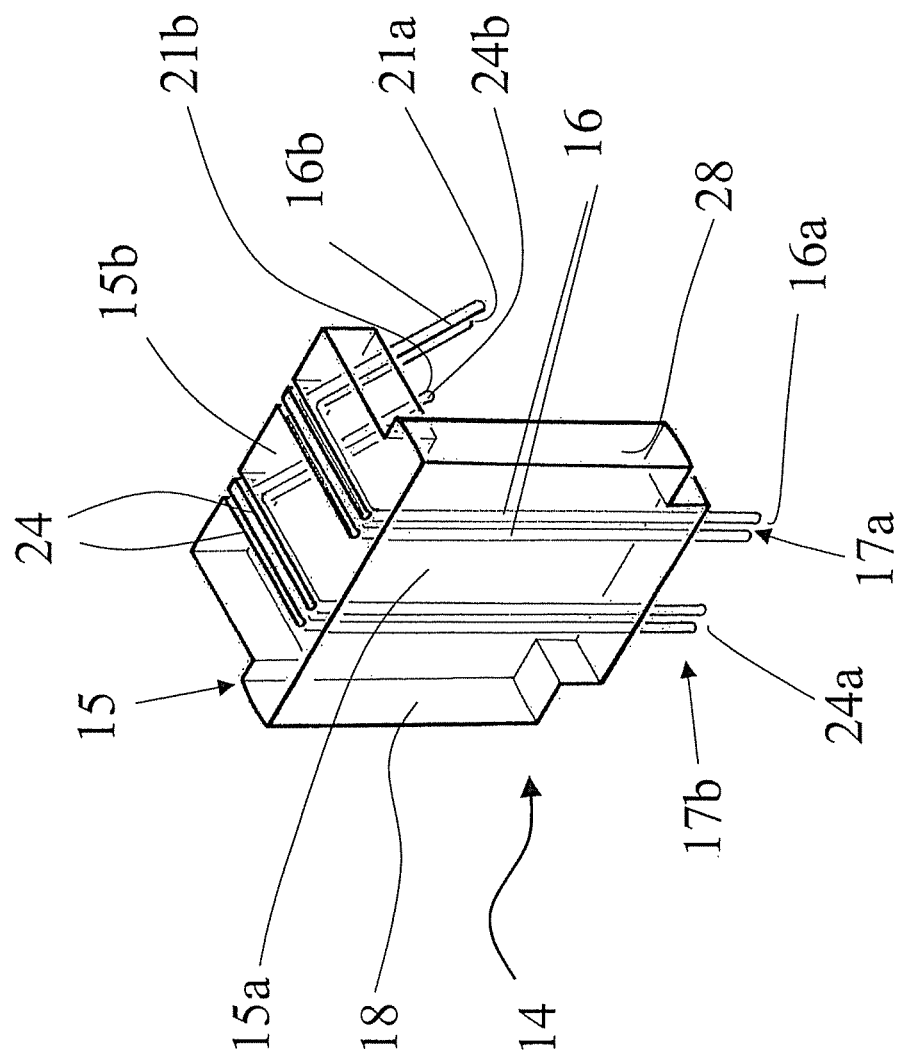
FIG. 2 is a perspective view of an electrode holder according to an embodiment of the present invention (with double determination technique)

The other part of the cartridge device 20 is the electrode holder 14, illustrated in FIG. 2 in a perspective view according to a first embodiment of the present invention. The electrode holder 14 consists particularly of a plastic body 15, in which two tiny electrode wire pairs 16, 24 are incorporated. Each wire of a wire pair 16, 24 has preferably a diameter of about 0.1-0.5 mm, most preferably 0.3 mm.

The electrode holder 14 comprises especially a L-formed body 15 with a long part 15a and a short part 15b perpendicular to the long part 15a. At the face side of the long part 15a of the electrode holder 14 each electrode wire of the electrode pairs 16, 24 protrudes and forms a sensor portion 16a, 24a. For example, two sensor portions 16a or 24a form together a sensor unit 17a or 17b. During the analysis the sensor units 17a and 17b are completely immersed into the blood sample. The blood platelets adhere on the sensor portions 16a, 24a of the wire pairs 16, 24 and change the electrical impedance between said two wires of a respective wire pair 16 or 24. These measured impedance values can be compared with each other and/or with a predetermined threshold.

At the face side of the short part 15b of the electrode holder 14 each electrode wire of the electrode pairs 16, 24 protrudes under a predetermined angle, for example 50°, and forms a connector portion 16b, 24b, respectively.

The electrode holder 14 of this preferred embodiment comprises two linear independent sensor units 17a, 17b, each formed by an electrode wire pair 16, 24. The sensor units 17a, 17b are particularly placed symmetrically to each other at the face side of the long part 15a of the body 15 in order to ensure identical flow conditions around each wire pair and acceptable measurement results. Preferably the two wires of an electrode pair 16 (24) are positioned parallel to each other and parallel to the wires of another electrode pair 24 (16).

The electrode holder is preferably inexpensively produced by injection moulding. This requires to insert the wires of the electrode pairs 16, 24 into the mould and to extrusion-coat them by the resin. This poses the problem not to bend the thin wires by the high pressure in the injection mould. Also it is important to automate the process of placing the wires into the mould, thus allowing fully automated production and thus low costs. Preferably the wires are automatically placed into the mould from a roll, then extrusion coated and afterwards automatically taken out of the mould and then cut into the right dimensions. This also provides the advantage that cable on a roll is less expensive than pre-cut cable bars. It is advantageous to keep the wires under tension during the injection process in order to prevent bending of the thin wires.

It is also advantageous to keep the body 15 of the electrode holder 14 thin, as it is shown in FIG. 2. This leads to reduced pressure requirements in the injection process and thus also to a lower tendency to bend the wires of the electrode wire pairs 16, 24. A thickness of 1-5 mm of the body 15 is preferred most. The plastic material used for the electrode holder is preferably a blood compatible material such as polystyrene, PMMA or polyethylene, most preferably polystyrene.

The material selected for the electrodes or wires needs to fulfil several requirements. It should provide a low electrical resistance. This provides a good electrical connection of the wires in the connection portions 16b, 24b to plugs 22 or equivalent devices and in addition it provides a stronger signal of the analysis. In the sensor portions 16a, 24a the wires are coated by the activated platelets which enhances the electrical resistance between them. When wires of a lower resistance are applied this leads to a stronger resistance change when the wires are coated by the platelets compared to a material with lower conductivity. Materials with a high conductivity include for example copper and copper alloys (copper-silver alloy, copper-magnesium alloy).

However the wire material must also not oxidate when contacted to blood, even when different oxidating drugs are present. This requires the surface of the wires 15 to have a low tendency to oxidate. Such materials are for example precious metals such as platinum, gold, silver. The named materials with a high conductivity (copper and copper alloys) have a high tendency to oxidate. However the precious metals are too expensive to be used for the production of a single use cartridge. According to the present invention it was found that by coating a low cost wire material with a high conductivity (preferably a silver-copper alloy comprising 0.2-2% silver, most preferably 0.9% silver) with a precious material such as silver (preferably using a coating of 0.5-20 g/kg, most preferably 2 g/kg) a wire is obtained which is economical, which provides a good electrical impedance and which is also sufficiently resistant to oxidation during the analysis. Other coatings made of gold, platinum or other precious metals can be also applied.

The electrodes are preferably wires having a circular cross-section. The inventors have tested diameters between 0.1 mm and 0.50 mm. The signal turns out to become weaker with increasing diameter, so that the electrodes should be thin. The electrode holder is manufactured by injection moulding which requires tearproof rods, i.e. the rods should not be to thin. The optimal value for diameter of the electrodes which encompasses these two aspects turned out to be 0.3 mm.

The length of the ends of the electrodes which stand out of the electrode holder 14 is preferably 4 mm. The inventors have tested lengths between 2 mm and 6 mm. It turned out, that the longer the ends are, the weaker the signal becomes, so that short ends are preferred. However, when the ends become too short, the production of the electrode holder becomes more complicated, so that an optimal length is about 4 mm.

A spacing of 0.5-1 mm between the electrode wires was found to provide optimal signal and reproducibility.

The electrode wires are preferably bended two times as is best seen in FIGS. 3 and 4. This bending ensures that the ends of the electrodes form together with the jack portion 12 of the cell 9 a jack. In the present case the inventors use preferably a geometry consistent with the normed jack RJ12. This allows to use the standard RJ12 plug to connect the cartridge device 20 to an analyser just by putting the plug into the jack portion 18.

After the injection moulding process the wires 16, 24 are bended for example under an angle of at least 90° as shown in FIG. 3.

Afterwards the electrode holder 14 is connected to the cell 9 by guiding a guiding part 28 of the holder 14 in said respective guiding rails 13 of the funnel tube 11 of the cell 9 until it contacts the upper edge of the stopping wall 27.

Figure 5:
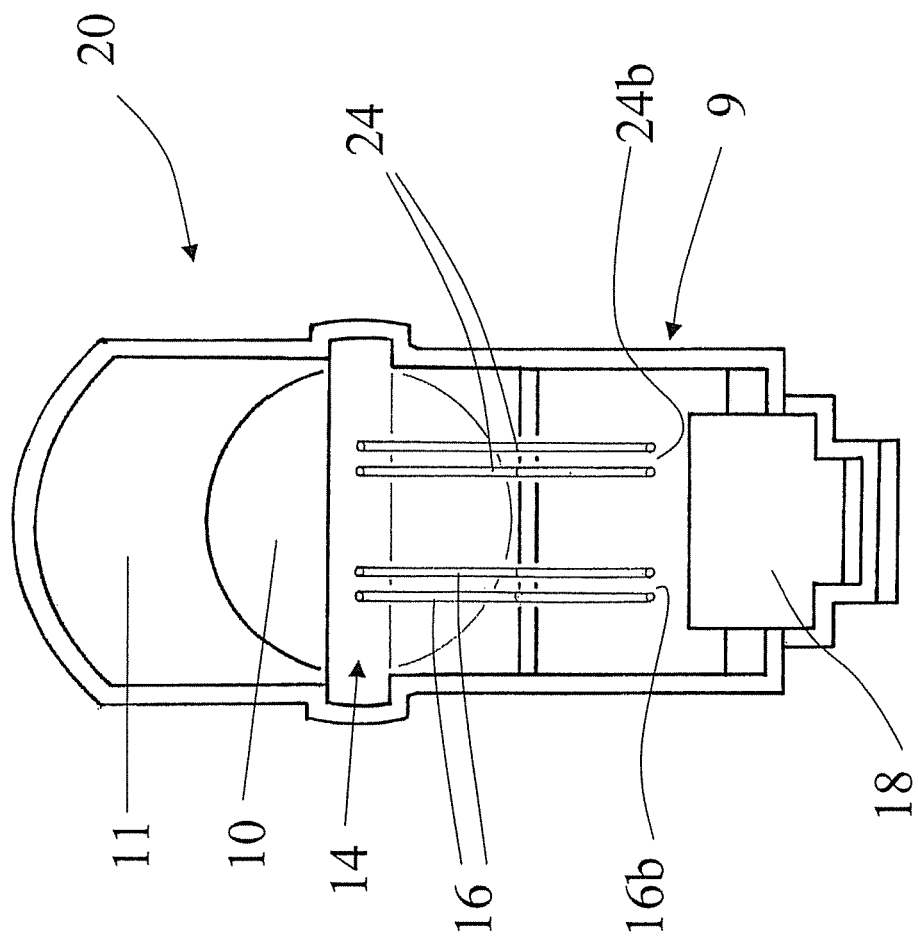
FIG. 5 is a top plan view of a cartridge according to a first embodiment of the present invention (with double determination technique)
Figure 6:
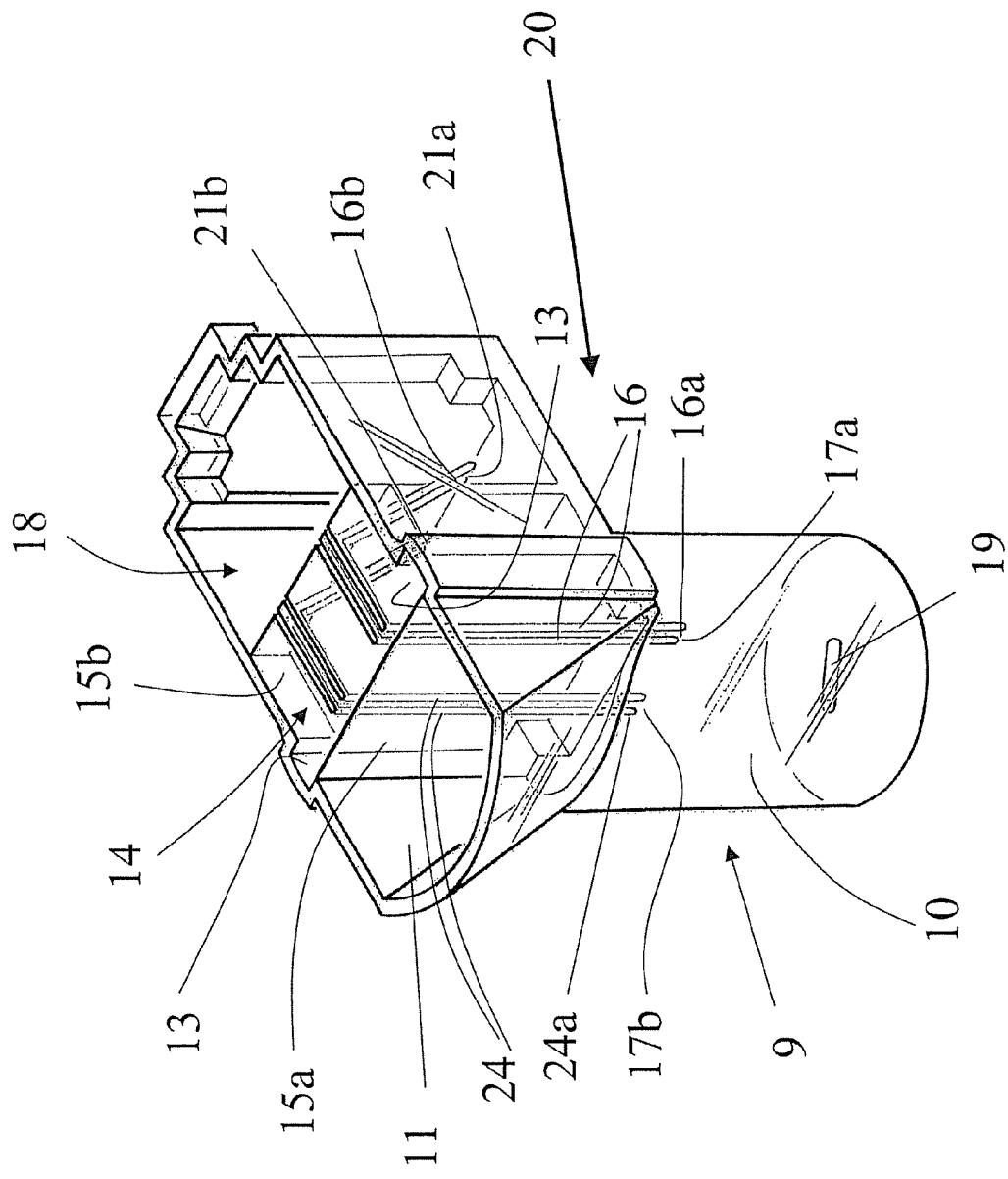
FIG. 6 is a perspective view of the cartridge according to the first embodiment of the present invention (with double determination technique)

FIGS. 4 to 6 illustrate an assembled cartridge device 20 in a sectional side view, a top plan view and a perspective view according to a preferred first embodiment of the present invention.

A magnetic or paramagnetic stir bar 19 for stirring the blood sample is placed into the cup portion 10. Then the whole device is packed into appropriate means for storage and shipping to the customer.

Before the analysis the user takes the cartridge device 20 out of the packaging and places it into an appropriate receptacle of the analyser. The receptacle is preferably heated to 37° to ensure that the analysis takes place under standardized and physiological temperature conditions.

The filling amount of the blood sample is preferably large enough to ensure that the ends of the electrode wires projecting from the face side of the long part 15a of the body 15 are completely covered.

Figure 7:
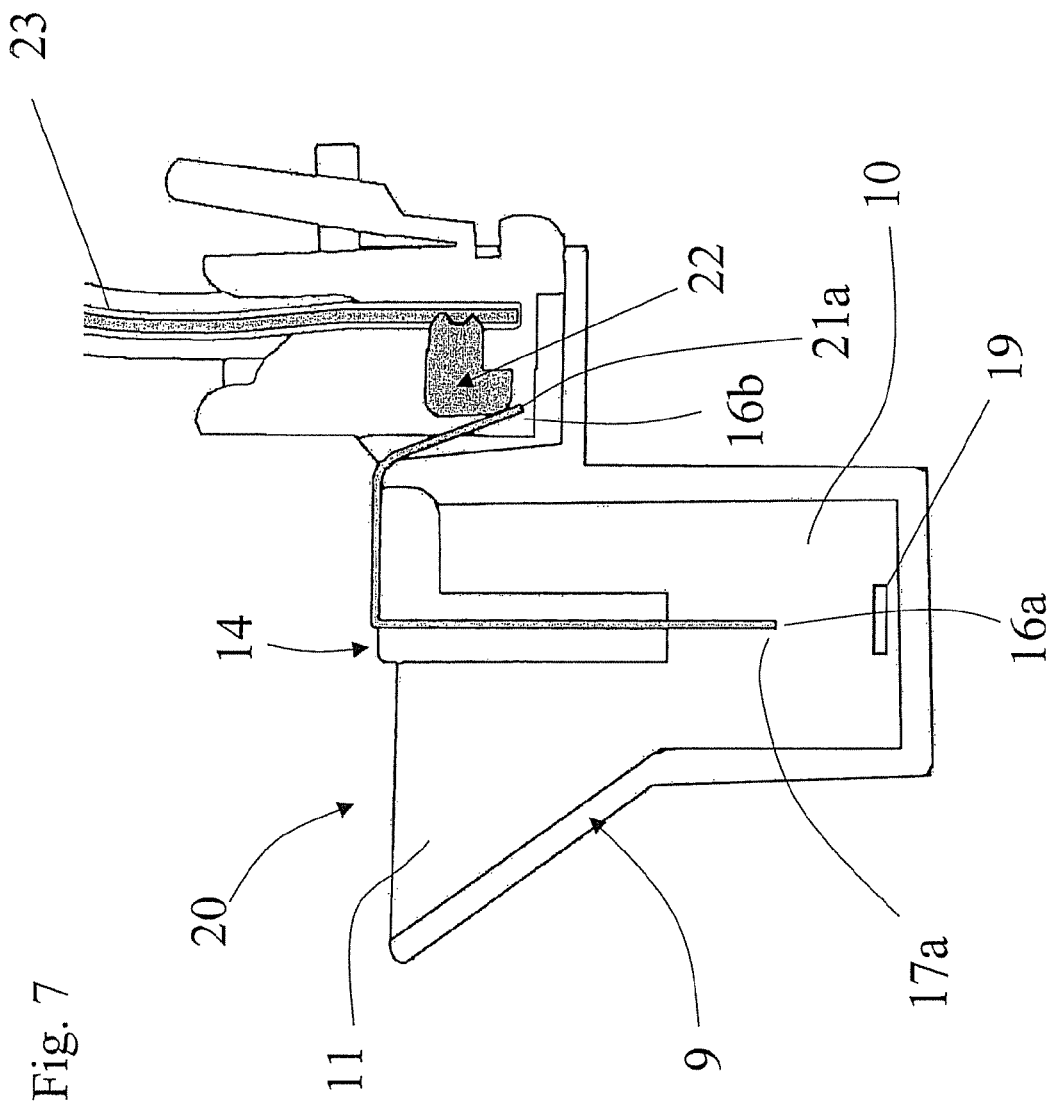
FIG. 7 is a sectional view of a cartridge device with attached plug and cable according to an embodiment of the present invention.

Appropriate means are placed under the receptacle that induce a stirring motion of the stir bar 19. The preferred means for stirring the sample is the use of electromagnets that are alternately turned on and off and therefore induce a rotation of the stir bar 19. The stir bar 19 can comprise a polytetrafluoroethylene (e.g., Teflon) coated stir bar, steel or siliconized steel. Siliconized stainless steel is the preferred material, as it is less expensive than polytetrafluoroethylene (e.g., Teflon) coated stir bars. Non-coated stir bars can alter the platelet activation due to the contact and adhesion of platelets to the thrombogenic steel material. Also permanent magnets that are rotated by adequate means or other means for inducing rotation of the sample (such as ultrasound, orbital movements of the cup) can be applied as obvious to a person skilled in the art The user then connects a plug 22, preferably a standard RJ12 plug, to the jack 18 as illustrated in FIG. 7, which shows a sectional view of an assembled cartridge device with a connected plug 22 according to a preferred embodiment of the present invention. The plug 22 is preferably a standard plug, which comprises particularly a conductive element 22 contacting the contact regions 16b, 24b, i.e. the plug portions 21a and 21b of the electrode wire pairs 16 and 24. The plug 22 is connected to an analyser (not shown) by means of a connection cable 23 and allows the signal of the analysis to be transferred from the cartridge device 20 to the analyser.

During the analysis the analyser continuously records the impedance change on both sensor units 17a and 17b. Under optimal conditions the impedance change of both sensor units 17a and 17b will be identical or nearly identical. However when due to material variations, dirt, damage of the wires 16, 24 during transport or other errors one sensor unit is defect, a strong variation is determined between the two sensor units 17a and 17b and the measurement is discarded. An automatic algorithm in the software distinguishes acceptable from non-acceptable variation between the results of the sensor units 17a and 17b and automatically stops the analysis if required. When an acceptable variation is recorded, for example the mean value of the two determinations is reported to the user. This leads to significantly improved precision. The rate of wrong diagnosis is significantly decreased compared to single analysis units.

After the analysis the user disconnects the plug 22 from the cartridge device 20 and discards it.

Linear Triple Cartridge Device

Figure 8:
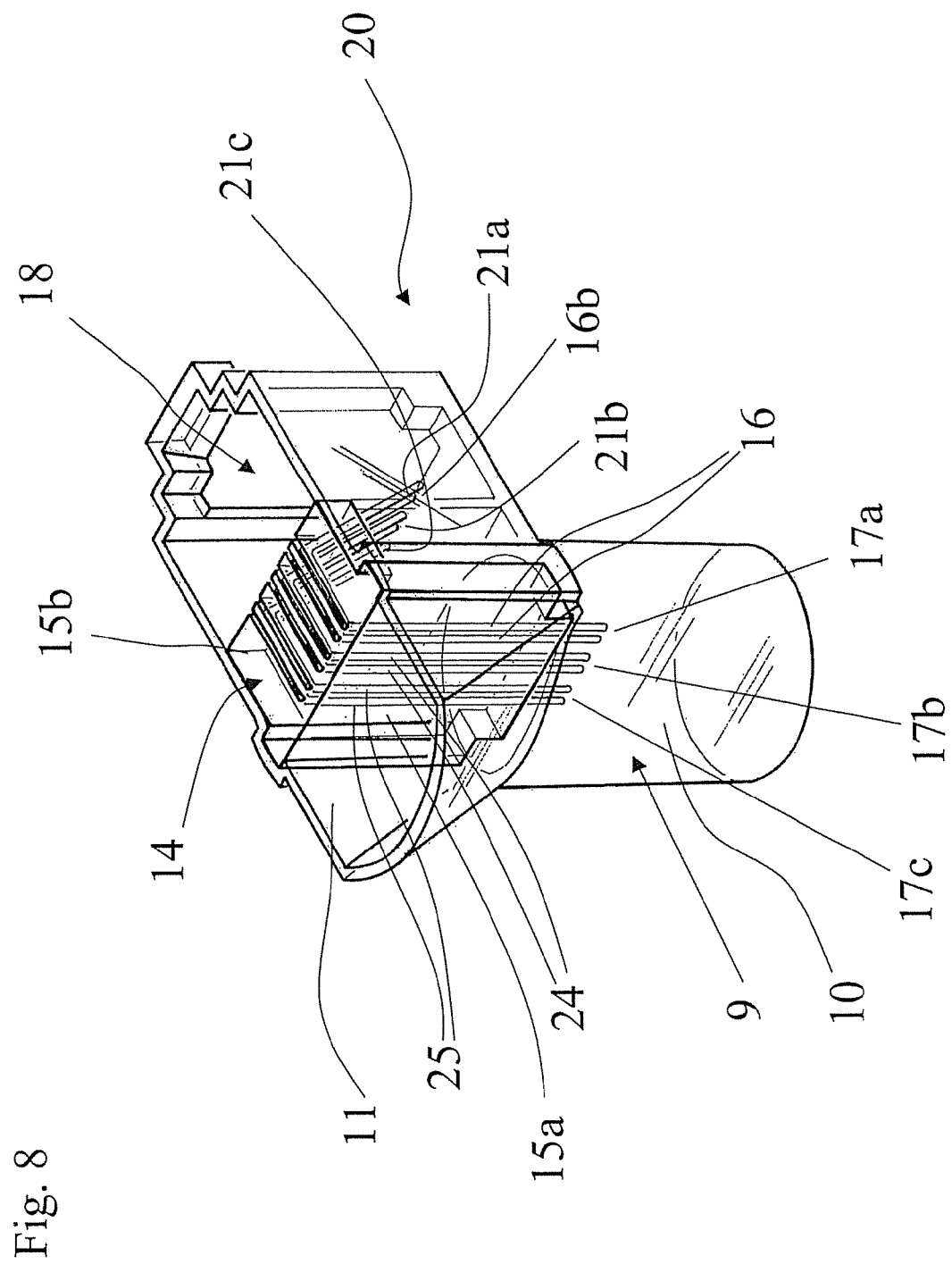
FIG. 8 is a perspective view of a cartridge device according to a second embodiment of the present invention (with triple determination technique.

A second preferred embodiment of the cartridge device 20 is shown in FIG. 8, which is a perspective view. The cell 9 according to the second embodiment is identical to the previous embodiment and therefore it is referred to the above evaluations.

However contrary to the first embodiment the electrode holder 14 according to the second embodiment comprises three sensor units 17a, 17b, 17c, which are linearly arranged to each other. Each sensor unit consists of a pair of electrode wires 16, 24 and 25, respectively. Due to the linear arrangement the electrode wire pair 24 is in the middle of the two remaining electrode wire pairs 16 and 25 and is exposed to a significantly lower blood flow when compared to the outer electrode wire pairs 16 and 25. Hence according to the second embodiment it is possible to compare platelet adhesion and aggregation under varying flow conditions. It is obvious to a person skilled in the art that by variations of the number and geometric arrangement of the test units the flow conditions under which the platelets are analysed can be varied and also differentiated software algorithms can be applied.

Linear Quadruple Cartridge Device

Figure 9:
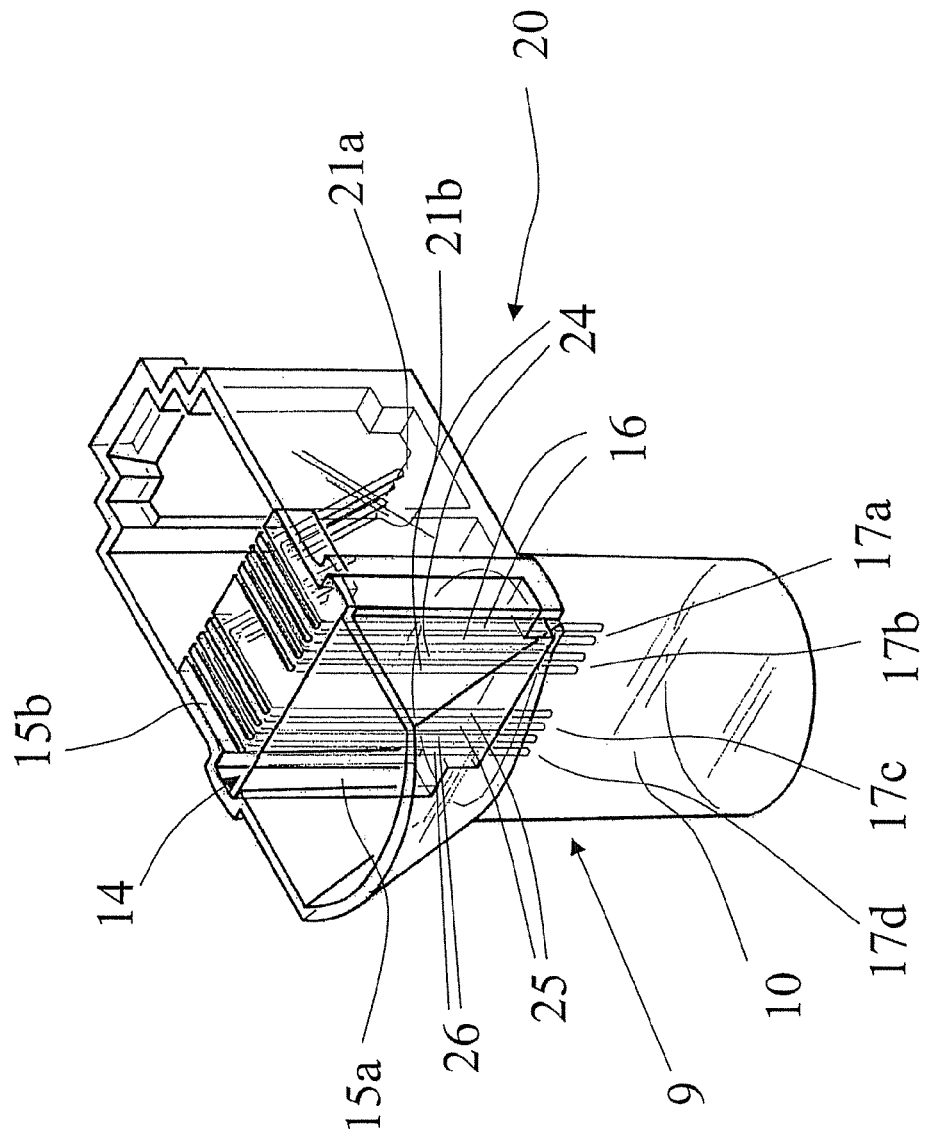
FIG. 9 is a perspective view of a cartridge device according to a third embodiment of the present invention (with linear quadruple determination technique)

According to a third preferred embodiment as shown in a perspective view in FIG. 9, the cell 9 is identical to the previous embodiments and therefore it is referred to the above evaluations.

However the electrode holder 14 according to the third embodiment comprises four sensor units 17a, 17b, 17c, 17d. These sensor units are linearly arranged to each other. Each sensor unit 17a, 17b, 17c and 17d consists of a pair of electrode wires 16, 24, 25 and 26, respectively. Due to the linear arrangement the middle two electrode wire pairs 24 and 25 are exposed to a lower blood flow compared to the outer electrode wires 16 and 26. Hence according to the third embodiment it is possible to make a double-determination of the platelet aggregation under low and high blood flow conditions, referring to the flow conditions of blood in vessels with small and large diameter.

Circular Triple Cartridge Device

Figure 10:
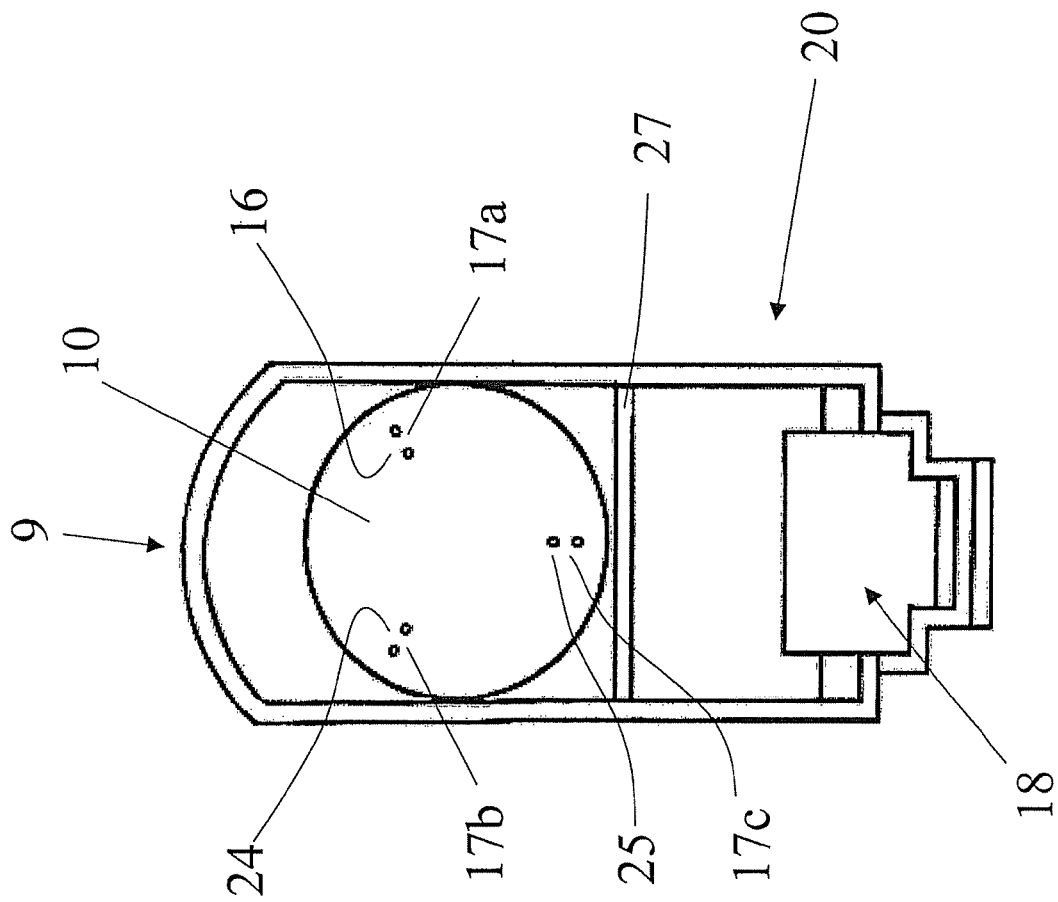
FIG. 10 is a top plan view of a cartridge device according to a fourth embodiment of the present invention (with circular triple determination technique.

FIG. 10 illustrates a top plan sectional view of a cartridge device 20 according to a fourth embodiment of the present invention. The cell 9 is identical to the aforementioned embodiments and therefore it is referred to the above evaluations.

However the electrode holder 14 is formed to allow a circular arrangement (FIG. 8) of several sensor units. According to the present arrangement shown in FIG. 10 three sensor units 17a, 17b and 17c are arranged at the same radial location in the blood sample, i.e. in the receiving portion 10, and exposed to the identical or nearly identical blood flow, which allows to directly compare the signals.

According to the fourth embodiment the analyser independently records the changes in conductivity between the wire pairs of the three sensor units 17a, 17b and 17c. Thus three independent results are obtained. For example the mean or median value is reported to the user, resulting in an enhanced precision of the analysis when compared to the prior art and to inventive embodiments containing only two independent sensor units.

Surface-Coated Punched Electrodes

Figure 11B:
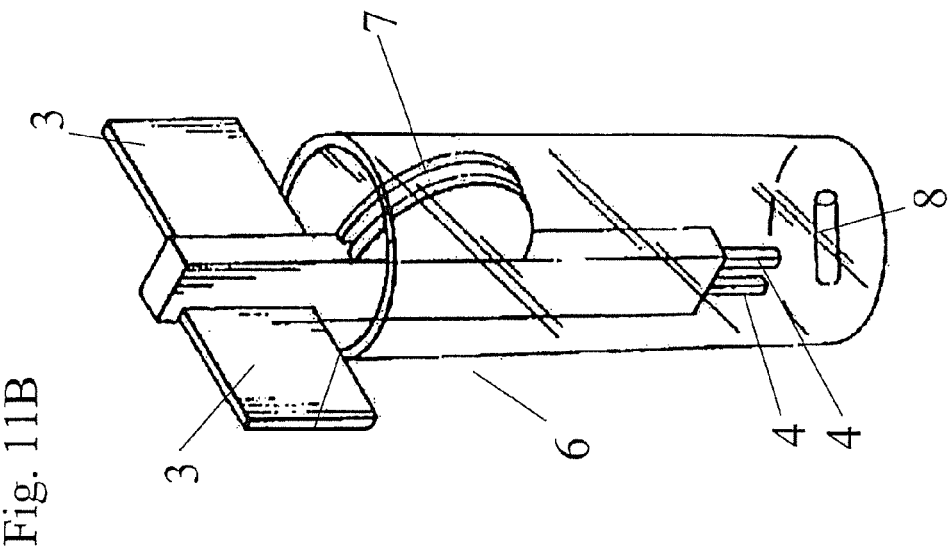
FIG. 11B is an perspective view of a cartridge device according to the prior art.
Figure 11A:
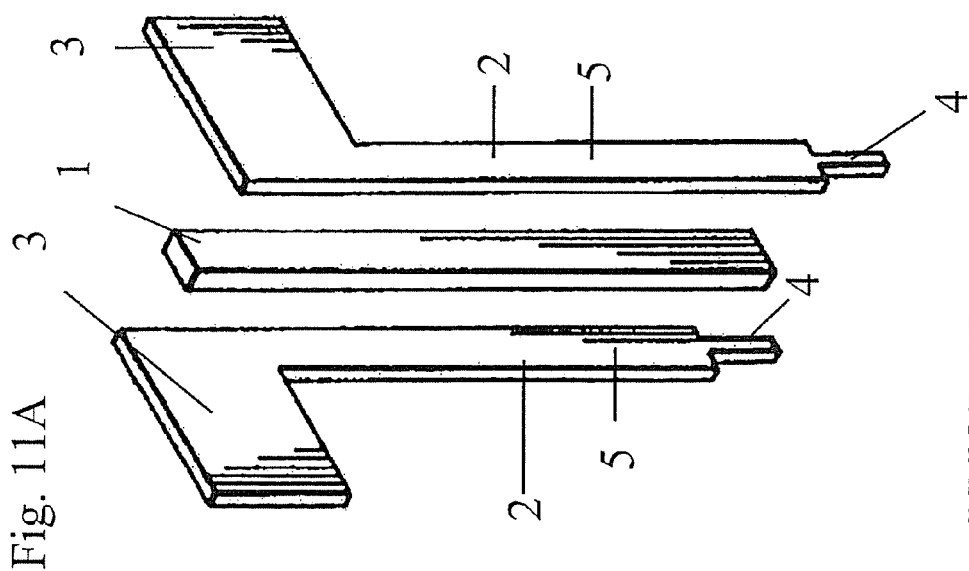
FIG. 11A is an explosive view of a part of a cartridge device according to the prior art.

According to another preferred embodiment a cartridge device is provided, wherein the electrodes are formed by punched metal (as shown in FIG. 11A), especially by using a highly electrically conductive material such as copper or copper alloys. The surface is coated using a precious material with a high conductivity, such as silver, gold or platinum. This allows to correct the aforementioned poor surface quality of the punched material by the coating with the precious material. In addition the high conductivity of the used metal material (e.g. copper) improves the signal of the analysis by the higher conductivity reduction when the electrode surface is coated by the activated platelets.

Multiple Punched Electrodes

According to another preferred embodiment a cartridge device is provided, wherein at least three electrodes made of punched metal are in contact with the blood. The shape of the electrodes can be similar to the shape of the electrodes shown in FIG. 11A. At least two separate measurements of conductivity are parallel performed. In case three electrodes are used, the conductivity between electrode 1 and electrode 2 is measured as signal 1. The conductivity between electrode 2 and 3 is used as signal 2. And the conductivity between electrode 3 and electrode 1 is used as signal 3. In case the variation of a determined conductivity signal is higher than an acceptable threshold (preferably 20%) of the mean value of the three signals, this signal is rejected and only the two other signals are analysed. In case also the conductivity of the remaining two signals shows a variation being too high, the whole analysis is discarded and the user is instructed to repeat the analysis. In case the signal variation is acceptable, the mean value or median value of the signals is reported to the user. This allows a significantly reduced probability of wrong determinations and also a reduced variation of the results.

Hence the present invention provides a cartridge device which solves several problems. On the one hand the limited reproducibility of previous methods according to the prior art for the measurement of aggregation in whole blood is eliminated. On the other hand a cartridge is provided which is accurate and so economical to produce that it can be discarded after each test.

Another advantage of the present invention is due to the fact that a cartridge which can be manufactured ready to use is provided, so that the application of the technique is simple and contains only few user-related sources of error and variation.

While the forgoing description and examples set forth specific illustrations of the practice of the present invention, those illustrations are intended to be representative only. Thus it will be apparent that numerous modifications and variations upon the designs and processes particularly described herein may be resorted to by those skilled in the art within the scope of the appended claims.

For example instead of the electrode wire pairs of the first to third embodiments several single electrodes or electrode wires can be used to receive several independent and separate measurement results.

It is obvious to a person skilled in the art that the wire sections 16b, 24b, 25b and 26b can serve as a plug or a jack in order to allow a connection to an analyser.

REFERENCE NUMERAL LIST 1 insulator
2 electrode
3 connection tap
4 tip
5 shaft
6 cuvette
7 clip
8 stir bar
9 cell
10 receiving portion/cup portion
11 tunnel tube
12 jack portion
13 guiding rail
14 electrode holder
15 plastic body
15a long part of body
15b short part of body
16 first electrode wire pair
16a sensor portion
16b connection portion
17a first sensor unit
17b second sensor unit
17c third sensor unit
17d fourth sensor unit
18 jack
19 stir bar
20 cartridge device
21a plug portion
21b plug portion
21c plug portion
21d plug portion
22 plug
23 connection cable
24 second electrode wire pair
24a sensor portion
24b connection portion
25 third electrode wire pair
25a sensor portion
25b connection portion
26 fourth electrode wire pair
26a sensor portion
26b connection portion
27 stopping wall
28 guiding part

The invention claimed is:

1. A cartridge device for conducting platelet aggregation analysis, comprising:
a cell having a receiving portion for receiving a blood sample;
a stirring device for circulating said blood sample within said receiving portion;
an electrode holder having at least two sensor units, wherein each sensor unit comprises at least two electrodes for measuring the electrical impedance between the at least two electrodes within the blood sample in at least two different locations; and
an analyser for comparing the electrical impedances measured by each one of the at least two sensor units in each of the at least two different locations in the blood sample in order to determine whether an acceptable or a non-acceptable variation in the impedance measurements exists, wherein the analyser stops an analysis of platelet aggregation when a non-acceptable variation is indicated, and reports a mean value of the impedance measurements by the at least two sensor units when an acceptable variation is indicated;
wherein the electrode holder is attached to the cell such that one end of each one of the at least two electrodes forming one of the sensor units for measuring the electrical impedance between the at least two electrodes is within the blood sample and that the opposite end of each one of the at least two electrodes is connectable to the analyser;
wherein the at least two electrodes consist of a metal comprising a first material comprising at least one of copper and copper alloy, which is covered by a second material comprising at least one of silver, platinum, and gold.

2. The cartridge device according to claim 1, wherein the first material is a copper-silver alloy.

3. The cartridge device according to claim 2, wherein the copper-silver alloy comprises 0.2 to 2% silver.

4. The cartridge device according to claim 2, wherein the copper-silver alloy comprises 0.9% silver.

5. The cartridge device according to claim 1, wherein the second material is a silver coating with a mass coverage in the range of 0.5 to 20 g/kg.

6. The cartridge device according to claim 1, wherein the second material is a silver coating with a mass coverage of about 2 g/kg.

7. The cartridge device according to claim 1, wherein the at least two electrodes stand out of the electrode holder between 2 mm and 6 mm.

8. The cartridge device according to claim 1, wherein the at least two electrodes have a spacing between them of between 0.5 mm and 1 mm.

9. A cartridge device for conducting platelet aggregation analysis, comprising:
a cell having a receiving portion for receiving a blood sample;
a stirring device for circulating said blood sample within said receiving portion;
an electrode holder having at least two sensor units, wherein each sensor unit comprises at least two electrodes for measuring the electrical impedance in the blood sample in at least two different locations; and
an analyser for comparing the electrical impedances measured by each one of the at least two sensor units in each of the at least two different locations in the blood sample in order to determine whether an acceptable or a non-acceptable variation in the impedance measurements exists, wherein the analyser stops an analysis of platelet aggregation when a non-acceptable variation is indicated, and reports a mean value of the impedance measurements by the at least two sensor units when an acceptable variation is indicated;
wherein the electrode holder is attached to the cell such that one end of the at least two electrodes forming one of the at least two sensor units for measuring the electrical impedance between the at least two electrodes within is in the blood sample and that the opposite end of the at least two electrodes is connectable to the analyser;

wherein the at least two electrodes consist of a metal comprising a first material comprising at least one of copper and copper alloy, which is covered by a second material comprising at least one of silver, platinum and gold; and wherein the at least two electrodes stand out of the electrode holder between 2 mm and 6 mm.

10. The cartridge device according to claim 9, wherein the first material is a copper-silver alloy.

11. The cartridge device according to claim 10, wherein the copper-silver alloy comprises 0.2% to 2% silver.

12. The cartridge device according to claim 10, wherein the copper-silver alloy comprising 0.9% silver.

13. The cartridge device according to claim 9, wherein the second material is a silver coating with a mass coverage in the range of 0.5 to 20 g/kg.

14. The cartridge device according to claim 9, wherein the second material is a silver coating with a mass coverage of about 2 g/kg.

15. The cartridge device according to claim 9, wherein the at least two electrodes have a circular cross section and have a diameter between 0.1 mm and 0.50 mm.

16. The cartridge device according to claim 9, wherein the at least two electrodes have a spacing between them of between 0.5 mm and 1 mm.

17. A cartridge device for conducting platelet aggregation analysis, comprising:
   a cell having a receiving portion for receiving a blood sample;
   a stirring device for circulating said blood sample within said receiving portion;
   an electrode holder having at least two sensor units, wherein each sensor unit comprises at least two electrodes for measuring the electrical impedance in the blood sample in at least two different locations; and
   an analyser for comparing the electrical impedances measured by each one of the at least two sensor units in each of the at least two different locations in the blood sample in order to determine whether an acceptable or a non-acceptable variation in the impedance measurements exists, wherein the analyser stops an analysis of platelet aggregation when a non-acceptable variation is indicated, and reports a mean value of the impedance measurements by the at least two sensor units when an acceptable variation is indicated;
   wherein the electrode holder is attached to the cell such that one end of the at least two electrodes forming one of the at least two sensor units for measuring the electrical impedance between the at least two electrodes within the blood sample and that the opposite end of the at least two electrodes is connectable to the analyser;
   wherein the at least two electrodes consist of a metal comprising a first material comprising at least one of copper and copper alloy, which is covered by a second material comprising at least one of silver, platinum and gold; and
   wherein the at least two electrodes have a spacing between them of between 0.5 mm and 1 mm.

18. The cartridge device according to claim 17, wherein the first material is a copper-silver alloy, and wherein the copper-silver alloy comprises 0.2% to 2% silver.

19. The cartridge device according to claim 17, wherein the second material is a silver coating with a mass coverage in the range of 0.5 to 20 g/kg.

20. The cartridge device according to claim 17, wherein the at least two electrodes have a circular cross section and have a diameter between 0.1 mm and 0.50 mm.

21. The cartridge device according to claim 17, wherein the at least two electrodes stand out of the electrode holder between 2 mm and 6 mm.

* * * * *